United States Patent [19]

Almond et al.

[11] Patent Number: 5,639,649

[45] Date of Patent: *Jun. 17, 1997

[54] ATTENUATED VIRUSES

[75] Inventors: Jeffrey William Almond, Reading; Philip David Minor, Herts; Michael Anthony Skinner, Cambridge, all of United Kingdom; Colin Ruaraidh Young, College Station, Tex.

[73] Assignee: Brtish Technology Group Limited, London, United Kingdom

[*] Notice: The term of this patent shall not extend beyond the expiration date of Pat. No. 5,298,416.

[21] Appl. No.: 386,652

[22] Filed: Feb. 10, 1995

Related U.S. Application Data

[63] Continuation of Ser. No. 205,145, Mar. 2, 1994, abandoned, which is a continuation of Ser. No. 18,549, Feb. 16, 1993, abandoned, which is a continuation of Ser. No. 721,442, Jul. 16, 1991, abandoned.

[30] Foreign Application Priority Data

Jan. 18, 1989 [GB] United Kingdom ................. 8901094

[51] Int. Cl.$^6$ ................. C12N 7/01; C12N 7/04; C12N 15/01; C12N 15/09
[52] U.S. Cl. ................. 435/235.1; 424/93.6; 435/172.3; 435/236
[58] Field of Search .................. 435/172.3, 235.1, 435/236; 424/93.6

[56] References Cited

U.S. PATENT DOCUMENTS 5,298,416 3/1994 Almond et al. ..................... 435/236

OTHER PUBLICATIONS

P.N. Borer et al. "Stability of ribnucleic acid double-stranded helices" J. Mol. Biol. (1974) 86, pp. 843–853.

W. Salser. "Globin mRNA sequences: analysis . . . " Cold Spring Harbor 42, (1977), pp. 985–1002.

S.M. Freier et al. "Improved free energies for B C base--pairs" J. Mol. Biol. (1985) 185, pp. 645–647.

Tinoco et al. (1973), Nature New Biol. 246: 40–41.

Freier et al. (1986). Proc. Natl. Acad. Sci USA 83:9373–9377.

*Primary Examiner*—Mindy Fleisher
*Assistant Examiner*—Nancy J. Degen
*Attorney, Agent, or Firm*—Nixon & Vanderhye

[57] ABSTRACT

An attenuated enterovirus or rhinovirus, suitable for use as a vaccine, has a reversed base pairing in the part, or in a part corresponding to the part, of the 5' non-coding region of the genome of poliovirus type 3 Leon strain shown below:

```
    471    477    483
 ...UCC...CCAUGGA...
 ...AGG...GGUGCCU...
    538    534    528
```

A suitable attenuated poliovirus has the bases G and C at positions 469 and 534 respectively for a type 1 or type 2 poliovirus or at positions 472 and 537 respectively for a type 3 poliovirus.

9 Claims, No Drawings

ATTENUATED VIRUSES

This is a rule 60 continuation of application Ser. No. 08/205,145, filed 2 Mar. 1994, now abandoned, which is a continuation of application Ser. No. 08/018,549, filed 16 Feb. 1993, now abandoned, which is a continuation of application Ser. No. 07/721,442, filed 16 Jul. 1991, now abandoned.

This invention relates to the construction of vaccines against rhinoviruses and enteroviruses, particularly polioviruses, by the introduction of defined mutations into their genomes. These mutations attenuate the virulence of wild type viruses and can further attenuate existing live attenuated vaccine virus strains, thereby making them less likely to revert to virulence.

At the present time, the only vaccines routinely used against enterovirus and rhinovirus infections are those against poliomyelitis. Of these the live attenuated vaccines developed by Sabin in the 1950's have found greatest use throughout the world. Vaccine strains derived from each of the three poliovirus serotypes (P1, P2 and P3) were prepared by passage of wild type viruses in cell cultures and whole animals until attenuated strains were obtained. These attenuated viruses are substantially less able to cause poliomyelitis in humans than the original wild type strains. They are administered orally and replicate in the gut to induce a protective immune response.

Although these vaccines are generally regarded as safe, their use is associated with a low level of paralysis in vaccines. This is most often associated with type 2 and type 3 serotypes and rarely, if ever, with type 1. There is therefore a requirement for improved type 2 and type 3 vaccines which would be comparable in safety to the excellent type 1 strain. There is also a requirement for vaccines against other enteroviruses, e.g. echo, coxsackie and hepatitis A, and against rhinoviruses.

The Sabin vaccine strains were developed by essentially empirical procedures. The genetic basis of their attenuation is not properly understood. Over the past few years, however, scientists have employed a number of molecular biological techniques in an attempt to elucidate the mechanism by which the neurovirulence of these vaccine strains is reduced. Most of the work has concentrated on serotypes 1 and 3. For both of these the complete nucleotide sequences of the vaccine strains have been compared with those of their neurovirulent progenitors.

In the case of poliovirus type 1, the vaccine strain differs from its progenitor at 47 positions in the 7441 base genome (Nomoto et al, 1982, *Proc Natl Acad Sci USA* 79: 5793-5797). All of these are simple point mutations and 21 of them give rise to amino acid changes in virus coded proteins. Although several mutations are thought to contribute to the attenuation phenotype of the vaccine strain, direct evidence has been presented that the mutation of A to G at position 480 in the 5' non-coding region of the genome has a marked attenuating effect on the virus (Nomoto et al, 1987, UCLA *Symp Mol Cell Biol*, New Series, Vol 54 (Eds M. A. Brinton and R. R. Rueckert), 437-452, New York: Alan R. Liss Inc).

Anarogous studies on poliovirus type 3 reveal just 10 nucleotide sequence differences in the 7432 base genome between the vaccine and its progenitor strain (Stanway et al, 1984, *Proc Natl Acad Sci USA* 81: 1539-1543). Just three of these give rise to amino acid substitutions in virus encoded proteins. The construction of defined recombinants between the vaccine and its progenitor strain has allowed the identification of the mutations which contribute to the attenuation phenotype. One of these is at position 2034 and causes a serine to phenylalanine change in virus protein VP3.

The other mutation of interest is C to U at position 472 in the 5' non-coding region of the genome. This latter mutation has been observed to revert to the wild type C rapidly upon replication of the virus in the human gut (Evans et al, 1985, *Nature* 314:548-550). This reversion is associated with an increase in neurovirulence. C at position 472 has also been shown to be essential for growth of a mouse/human polio recombinant virus in the mouse brain (La Monica et al, 1986, *J Virol* 57:515-525). Recently, we have observed that at 481 in poliovirus type 2 A changes to G in an analogous fashion upon replication of the type 2 vaccine in the gut of vaccines.

In EP-A-0323900 attenuated enteroviruses in particular polioviruses, and rhinoviruses are described which have an attenuating mutation at a position which is, or corresponds with, position 479 or 482 of poliovirus type 3 Leon strain. The attenuated viruses may also have an attenuating mutation at position 472.

A new model for the secondary structure of the 5' non-coding RNA of poliovirus type 3 Leon strain has now been proposed by us (Skinner et al, 1989, *J. Mol. Biol*, 207, 379-392). In the model, bases in the region 470 to 540 are paired as follows:

```
    471      477      483
 ...UCC ...CCAUGGA...
 ...AGG ...GGUGCCU...
    538      534      528
```

We have found that a poliovirus with the base pair 472-537 reversed, i.e. 472 G and 537 C, is attenuated. Further, this attenuated virus has a slightly lower LD$_{50}$ value than the corresponding poliovirus which only has the mutation C to G at position 472 but which retains the wild-type G at position 537. There is no selective pressure on a poliovirus to mutate to a more attenuated poliovirus, so the attenuation in the double mutant poliovirus may be locked in.

The findings can be extrapolated to all polioviruses. Indeed, they may be extrapolated to other enteroviruses and rhinoviruses. Mutations resulting in the reversal of a base pair at sites of other enteroviruses and rhinoviruses corresponding to the positions shown above for poliovirus type 3 Leon strain can lead to attenuation. There is a relatively high degree of homology between the genome RNA of all enteroviruses and rhinoviruses. The positions of another strain of enterovirus or rhinovirus corresponding to the positions of poliovirus type 3 Leon strain (based on the numbering used in the Stanway et al paper already referred to) can be determined by lining up the sequences of the genomic RNA of the strains.

Accordingly the invention relates to attenuated enteroviruses and rhinoviruses in which there is a reversal of a base pairing in the part, or in a part corresponding to the part, of the 5' non-coding region of the genome of poliovirus type 3 Leon strain shown below:

```
    471      477      483
 ...UCC ...CCAUGGA...
 ...AGG ...GGUGCCU...
    538      534      528
```

The accompanying Figure (SEQ ID NO: 5 and SEQ ID NO: 6) shows the relevant part of the 5' non-coding region of poliovirus type 3 Leon strain in more detail. In accordance with the present invention, one or more of the base pairs 471/538, 472/537, 473/536, 477/534, 478/533, 479/532, 480/531, 481/530, 482/529 and 483/528 or of the corresponding base pairs of rhinoviruses or of other enteroviruses may be reversed.

The present invention is particularly applicable to polioviruses. The invention is typically applied to a virus responsible for a disease or illness in humans. An attenuated poliovirus may be a type 1, type 2 or type 3 poliovirus, for example a Sabin strain with a reversed base pairing according to the invention. Types 2 and 3 are preferred. For types 1 and 2, positions 468, 474, 480, 525, 531 and 535 correspond to positions 471, 477, 483, 528, 534 and 538 respectively of poliovirus type 3.

Any base pair may be reversed to obtain an attenuated virus. More than one base pair, for example 2 or 3 base pairs, may be reversed. We have found in particular that the double mutation C to G at position 472 and G to C at position 537 in the 5' non-coding region of poliovirus type 3 Leon strain causes attenuation. A useful attenuated. poliovirus therefore has the bases G and C at positions 472 and 537 respectively in the case of type 3 polioviruses or at positions 469 and 534 respectively in the case of type 1 or 2 polioviruses. Indeed a useful attenuated enterovirus or rhinovirus generally may have a reversed base pairing at the paired positions corresponding to positions 472 and 537 of poliovirus type 3 Leon strain.

In a separate aspect of the invention, there are provided attenuated enteroviruses, in particular polioviruses, and rhinoviruses having an attenuating mutation at feast at a position which is, or corresponds with, position 537 of the genome of poliovirus type 3 Leon strain. Optionally there is also an attenuating mutation at position 472.

Such an attenuated poliovirus may be a type 1, type 2 or type 3 poliovirus, for example a Sabin strain. Types 2 and 3 are preferred. For types 1 and 2, positions 469 and 534 correspond to positions 472 and 537 of poliovirus type 3 Leon strain. A useful attenuated poliovirus therefore has the base C at position 537 in the case of type 3 polioviruses or at position 534 in the case of types 1 and 2 polioviruses. Useful attenuated viruses with mutations at both positions 472 and 537 or at the corresponding positions are as described above.

An attenuated virus according to the invention is prepared by a process comprising:

(i) introducing the or each desired mutation by site-directed mutagenesis into a sub-cloned region, which includes the or each position it is wished to mutate, of a cDNA of an enterovirus or rhinovirus;

(ii) reintroducing the thus modified region into a complete cDNA from which the region was derived; and (iii) obtaining live virus from the cDNA thus obtained.

A mutation can be introduced into a strain of an enterovirus or rhinovirus, for example wild-type virus, by site-directed mutagenesis of its genomic RNA. This may be achieved beginning with sub-cloning the appropriate region from an infectious DNA copy of the genome of any of the virus strain, for example a vaccine strain or its progenitor, into the single strand DNA of a bacteriophage such as M13. The virus strain may be a neurovirulent strain but is preferably a vaccine strain. For poliovirus it may be a Sabin, type 3 Leon or type 1 Mahoney strain. The or each desired mutation is then introduced into this sub-cloned cDNA using the technique of oligonucleotide directed mutagenesis.

After the introduction of mutations, the modified sub-cloned cDNAs are reintroduced into the complete cDNA from which they were derived and, for virulence testing in mice, into a cDNA derived from a murine poliovirus deriva-tive known to cause a poliomyelitis type disease in mice (La Monica et al, 1986). Live virus is recovered from the mutated full length cDNA by production of a positive sense RNA typically using a T7 promoter to direct transcription in vitro (Van der Werf et al, 1986; *Proc Natl Acad Sci*, USA 83:2330–2334). The recovered RNA may be applied to tissue cultures using standard techniques (Koch, 1973, *Curr Top Microbiol Immunol* 61:89–138). After 4–6 days incubation virus can be recovered from the supernatant of the tissue culture. The level of neurovirulence of the modified virus may then be compared with that of the unmodified virus using a standard LD50 test in mice (La Monica et al, 1986) or the WHO approved vaccine safety test in monkeys (*WHO Tech Rep Set* 687:107–175, 1983).

The attenuated viruses can be used as vaccines. They may therefore be formulated as pharmaceutical compositions further comprising a pharmaceutically acceptable carrier or diluent. Any carrier or diluent conventionally used in vaccine preparations may be employed. For example, the presently used live attenuated poliovirus strains are stabilised in a solution of 1 molar $MgCl_2$ and administered as a mixture of the three serotypes.

The attenuated viruses can therefore be used to prevent an infection attributable to an enterovirus or rhinovirus in a human patient. For this purpose, they may be administered orally, as a nasal spray, or parenterally, for example by subcutaneous or intramuscular injection. A dose corresponding to the amount administered for a conventional live virus vaccine, such as up to $10^6$ $TCID_{50}$ for a Sabin vaccine strain in the case of poliovirus, may be administered.

The following Examples illustrate the invention.

EXAMPLE 1

Construction of in vitro mutants

A synthetic T7 polymerase promoter was cloned into pBR322 in an EcoRI-Hind3 linker to give pBRT7. The linker included a StuI site 5' of the Hind3 site. The sequence from the T7 polymerase promoter to the StuI site of the resulting construct was:

TTC GAA ATT AAT ACG ACT CAC TAT AGG CCT (SEQ ID NO: 1).

This enabled sequences to be ligated to the T7 promoter so that only 2 extra Gs would be added to the 5' end of RNA transcripts. The extreme 5' end of pOLIO LEON (Stanway et al, 1984), which has a poly G tail and a PstI site as a result of the cDNA cloning procedure, was replaced by a linker of the sequence:

TAT GAC GCG TGC GGC CGC AAG CTT TAA AAC (SEQ ID NO: 2) . . . (polio 5' non-coding region) . . . $GGTAC_{70}$.

The 5' end was therefore limited by a Hind3 site, whilst the PstI site and the poly G tail were removed. A KpnI site, at position 70 in Leon, was used as the 3' end of the linker. Using this construction, the 5' end of pOLIO LEON from the Hind3 to a BamHI site (674), was cloned into pBRT7 to give pBRT75'L. The 5' non-coding region was brought under the control of the T7 promoter by digesting pBRT75'L with StuI and Hind3, making the Hind3 site blunt-ended using mung bean nuclease and religating to give p1–5 MBN. The resulting T7 promoter and 5' poliovirus sequence thus read:

TTCGAAATTAATACGACTCACTATAGGTTAAAC- (SEQ ID NO: 3).

An Sst I site at the 3' end of the hybrid poliovirus type 3 Leon/type 2 lansing sequence in pVN23 (La Monica et al, 1986) was removed by partial Sst I digestion, filling in by T4 polymerase and religation. Poliovirus sequences from this plasmid were then cloned into p1-5 MBN, following digestion of both plasmids with Mlul and Sall, to give pT7SFP. Infectious virus could be recovered by linearising pT7SFP with Sall, synthesis of full length RNA using T7 polymerase and transfection of Hela cells with the RNA using the DEAE dextran method (Van der Werf et al, 1986).

The template for in vitro mutagenesis was made by subcloning the 5' non-coding region of poliovirus type 3 Leon from pVN23 (La Monica et al, 1986) into the M13 derivative mICE 19 (Epernon, Nucl. Acids Res. 14, 2830, 1986), using the Hind3 and SstI sites. A mutation was then introduced into this subcloned DNA fragment using the technique of oligonucleotide-directed mutagenesis (Zoller and Smith, Nucl. Acids Res. 10, 6487–6500, 1982). The oligonucleotide used for construct MAS 27-7 was: CCA TGG TTA GCA TTA GCC GC (SEQ ID NO: 4).

Mutant 27-7 was constructed by hybridising this oligonucleotide to the single stranded cloned DNA fragment in the M13 phage derivative. The oligonucleotide is complementary to the target region except at the position to be mutated, where the base complementary to the desired mutation is incorporated. The hybridised M13 and oligonucleotide DNA were incubated in a reaction mixture containing DNA precursors and the enzymes DNA polymerase and DNA ligase. After incubation for one hour at 37° C., closed circular DNA was isolated from this mixture by agarose gel electrophoresis. This DNA was then used to transform *E. coli* mutS or mutL (deficient in DNA mismatch repair) which were then plated out on a lawn of *E coli* JM101.

M13 plaques which arose on this lawn of *E. coli* were picked and propagated and single stranded M13 phage DNA isolated. The DNAs were then sequenced using the method of Sanger and those with the desired mutation were identified. From these, batches of replicative form double stranded DNA were prepared and the Mlu1-Sst1 fragment containing 471 base pairs of infectious poliovirus cDNA, which incorporates the mutation, was recovered.

The mutated cDNA fragment was then reintroduced into pT7SFP. Live virus was recovered from the mutated full length cDNA by the production of a positive sense RNA transcript from the T7 promoter in vitro (Van der Werf et al, 1986) which was applied to Hela cells in tissue culture using standard techniques (Koch, 1973). After 4 to 6 days incubation a cytopathic effect was observed and virus could be recovered from the supernatant.

Recovered mutant virus 27-7 with a G at position 472 was plaque purified and propagated in Hela cells. This virus pool was used for the preparation of RNA on which the sequence of the virus mutant was verified using primer extension nucleotide sequencing (Evans et al, 1985). A portion of the pool was also used to assay neurovirulence.

Assessment of virulence for mice

Mutant virus 27-7 was grown in Hep2c cells, purified on sucrose gradients (Evans et al, 1985) and pelleted twice through phosphate buffered saline (PBS) before resuspension in PBA at $10^9$ pfu per ml. C57 black mice (obtained from OLAC), aged 21–28 days, were inoculated intracranially with 10–20 μl of virus. Virus dilutions examined were from $10^1$ to $10^7$ pfu per mouse in tenfold steps, and five or ten mice were used per dilution. Animals were observed once or twice a day for a period of up to 40 days post inoculation. The endpoint of the experiment for the determination of the $LD_{50}$ value was set at 21 days. The $LD_{50}$ value of mutant 27-7 was $>10^7$ pfu.

Animals were sacrificed when full flaccid paralysis of one or more limbs was evident, and stored at −20° C. until the brain was removed for virus isolation. The brain was homogenised in 10 ml PBS, clarified by low speed centrifugation and filtered through a 0.22 μm filter before inoculation of 4 ml onto $10^8$ Hep2c cells. Five viruses were recovered. The recovered viruses were designated 27 plaque 1A, 27 plaque 2A, 27.7A, 27.7B and 27.7C. Virus isolates were grown up, sequenced (Evans et al, 1985) and reinoculated into mice to determine their $LD_{50}$ values.

The $LD_{50}$ values and sequences are shown in Table 1 below, together with those for the original mutant 27-7 and for type 3 Leon. Differences between the base sequence for type 3 Leon and that for the other viruses are underlined.

TABLE 1

| Virus | $LD_{50}$ (pfu) | Sequence (470–475 . . . 535–539) |
|---|---|---|
| Leon | $10^1$ | A U C C U A . . . C G G A A |
| 27-7 | $>10^7$ | A U <u>G</u> C U A . . . C G G A A |
| 27 plaque 1A | $4 \times 10^5$ | A U <u>G</u> C U A . . . C G G A A |
| 27 plaque 2A | $10^3$ | |
| 27-7A | $10^2$ | A U C C U A . . . C G G A A |
| 27-7B | $10^1$ | A U C C U A . . . C G G A A |
| 27-7C | $10^6$ | A U <u>G</u> C U A . . . C G <u>C</u> A A |

These results show that mutant 27-7 is not a stable attenuated virus because viruses 27-7A and 27-7B, derived from 27-7, have back-mutated at position 472 to become. neurovirulent viruses having $LD_{50}$ values in the region of $10^1$–$10^2$ pfu. However, virus 27-7C has an $LD_{50}$ value of $10^6$ pfu and shows a compensating stabilising mutation at position 537. As can be seen from the accompanying Figure, bases 472 and 537 are paired. Virus 27-7C was deposited at the European Collection of Animal Cell Cultures, Porton Down, GB on 16 Jan. 1990 under accession number ECACC 90011604.

EXAMPLE 2

In an attempt to identify more 27.7C type viruses, parental virus 27.7 was again intracranially injected into mice. Viruses were recovered from animals displaying paralysis. The results are shown in Table 2.

TABLE 2

| Virus | Base at position: 472 | | | | | 537 |
|---|---|---|---|---|---|---|
| MAS 27.7 | | | | | | |
| 27.7 pl A | G | | | | | G |
| 27.7 A | C | | | | | G |
| 27.7 B | C | | | | | G |
| 27.7 C | G | | | | | C |
| 27.7 p 2A | C | | | | | G |
| 27.7 p 2A/1A | C | | | | | G |
| 27.7 p 2A/2A | C | | | | | G |
| 27.7 p 2A/3A | C | | | | | G |
| 27.7 P 2A/4A | C | | | | | G |
| 27.7 p 2A/4B | C | | | | | G |
| 27.7 D | C | T<br>489 | T<br>492 | A<br>494 | A<br>498 | G |
| 27.7 E | C | | | | | G |
| 27.7 F | C | | | | | G |

One 27.7C type virus was isolated from a group of 13 such recovered viruses. In a further attempt to identify more 27.7C type viruses, virus 27 plaque 1A (same sequence of 5' non-coding region as the parental 27.7 virus) was injected intracranially into mice. Viruses were recovered from animals displaying paralysis. The results are shown in Table 3.

TABLE 3

| Virus | Base at position: 472 | 537 |
|---|---|---|
| 27 pl 1A | G | G |
| 27 pl 1A/1C | C | G |
| 27 pl 1A/1B | C | G |
| 27 pl 1A/2B | G | C |
| 27 pl 1A/2C | C | G |
| 27 pl 1A/3A | G | C |
| 27 pl 1A/3B | C | G |
| 27 pl 1A/4A | C | G |
| 27 pl 1A/5B | G | C |
| 27 pl 1A/6A | C | G |
| 27 pl 1A/7B | C | G |
| 27 pl 1A/7C | C | G |

A further three 27.7C type viruses were isolated from a group of 12 recovered viruses. These 27.7C type viruses have been designated 27 pl 1A/2B, 27 plaque 1A/3A and 27 pl 1A/5B.

It was hoped that when this virus 27.7C was passaged many times through mice that the $LD_{50}$ value of this virus would be maintained at $10^6$–$10^7$ p.f.u. Indeed, it is shown in Table 4 below that when 27.7C virus was passaged for a further generation in mice (27.7C/2A-7D) that all 9 recovered viruses from mice displaying paralysis were base paired attenuating polioviruses (G at 472 and C at 537).

TABLE 4

| Virus | Base at position: 472 | 537 |
|---|---|---|
| MAS 27.7 | G | G |
| 27.7 C/2A | G | C |
| 27.7 C/2B | G | C |
| 27.7 C/4A | G | C |
| 27.7 C/5A | G | C |
| 27.7 C/5B | G | C |
| 27.7 C/6A | G | C |
| 27.7 C/7A | G | C |
| 27.7 C/7C | G | C |
| 27.7 C/7D | G | C |
| 27.7 C/2A/7A | G | C |
| 27.7 C/2A/7C | G | C |
|  | ALL G | ALL C |

These 27.7C type viruses have now been passaged for a further three generations in mice. All polioviruses recovered from paralysed animals were base paired attenuating ($LD_{50} > 10^6$ p.f.u.) polioviruses (G at 472 and C at 537). Some of our most recent data on the passage of these 27.7C polioviruses in mice is summarised in Table 5 below.

TABLE 5

| Virus | Base at position: 472 | 537 | $LD_{50}$ |
|---|---|---|---|
| 27.7 Parental Virus | G | G | $8.25 \times 10^6$ |
| 27.7C (3 Viruses) | G | C | $2.63 \times 10^6$ |
| 27.7C/2A-7D) (9 Viruses) | G | C | $2.57 \times 10^6$ |
| 27.7C/2A/3A-7B (4 Viruses) | G | C | $5.43 \times 10^6$ |

EXAMPLE 3

Protective Immunity Elicited by 27.7C Type Virus

In a series of experiments groups of C57BL/6 mice were injected intracranially with $10^1$–$10^7$ p.f.u. of a 27.7C virus. Animals were then observed daily for paralysis up to Day 50. surviving non-paralysed mice were then bled out and sera assayed for levels of neutralising antibody to Lansing poliovirus. The results for three attenuated stable base paired 27.7C type viruses are shown in Tables 6 to 8.

TABLE 6

Neutralising antibody elicited by 27.7C/2A/5B virus

| Day Number | Virus Titre-Injected | Antibody Titre to Lansing | Paralysed or Non-Paralysed |
|---|---|---|---|
| 25 | $10^7$ | 32 | Non-Paralysed |
| 25 | $10^7$ | 64 | Non-Paralysed |
| 26 | $10^6$ | >256 | Non-Paralysed |
| 26 | $10^6$ | 16 | Non-Paralysed |
| 27 | $10^5$ | 128 | Non-Paralysed |
| 28 | $10^5$ | 16 | Non-Paralysed |
| 28 | $10^5$ | < | Non-Paralysed |
| 29 | $10^5$ | < | Non-Paralysed |
| 29 | $10^5$ | 8 | Non-Paralysed |
| 37 | $10^4$ | < | Non-Paralysed |
| 37 | $10^4$ | < | Non-Paralysed |
| 38 | $10^4$ | < | Non-Paralysed |

TABLE 7

Neutralising Antibody Elicited by 27.7C/2A/7C Virus

| Day Number | Virus Titre-Injected | Antibody Titre to Lansing | Paralysed or Non-Paralysed |
|---|---|---|---|
| 27 | $10^7$ | 128 | Non-Paralysed |
| 30 | $10^6$ | 8 | Non-Paralysed |
| 31 | $10^6$ | 32 | Non-Paralysed |
| 32 | $10^6$ | 64 | Non-Paralysed |
| 32 | $10^6$ | 128 | Non-Paralysed |
| 33 | $10^5$ | >256 | Non-Paralysed |
| 33 | $10^5$ | 8 | Non-Paralysed |
| 34 | $10^5$ | 2 | Non-Paralysed |
| 34 | $10^5$ | 4 | Non-Paralysed |
| 35 | $10^4$ | < | Non-Paralysed |

TABLE 8

Neutralising Antibody Elicited by 27.7C/2A/7D Virus

| Day Number | Virus Titre-Injected | Antibody Titre to Lansing | Paralysed or Non-Paralysed |
|---|---|---|---|
| 39 | $10^7$ | 128 | Non-Paralysed |
| 39 | $10^7$ | 64 | Non-Paralysed |
| 40 | $10^7$ | 64 | Non-Paralysed |
| 40 | $10^7$ | 64 | Non-Paralysed |
| 41 | $10^6$ | 16 | Non-Paralysed |
| 41 | $10^6$ | 64 | Non-Paralysed |
| 43 | $10^5$ | < | Non-Paralysed |
| 43 | $10^5$ | 128 | Non-Paralysed |
| 44 | $10^5$ | 2 | Non-Paralysed |
| 45 | $10^4$ | < | Non-Paralysed |
| 45 | $10^4$ | < | Non-Paralysed |
| 46 | $10^4$ | < | Non-Paralysed |

EXAMPLE 4

Multiple copies of 27.7C virus genome obtained by polymerase chain reaction (PCR)

p27.7C PCR was constructed using DNA obtained from the 27.7C virus using polymerase chain reaction. An oligonucleotide complimentary to the nucleotides 761–783 of poliovirus type 3 was used to reverse transcribe RNA extracted from purified 27.7C virus. A second oligonucleotide homologous to nucleotides 36–60 was then used to amplify the region of 27.7C between nucleotides 36–783 which contains the CG to GC mutation responsible for the attenuation of revertant 27.7C. This PCR amplified DNA was digested with MluI and SstI and cloned into pt7SFP (Skinner et al *J. Mol. Biol.* 207, 379–392, 1989), following digestion of the plasmid with MluI and SstI, to give p27.7C PCR.

The p27.7C PCR sequence was checked between the MluI and SstI cloning sites by double stranded DNA sequencing.

Infectious virus was recovered by linearising p27.7C PCR with SalI, synthesising full length RNA by T7 polymerase and transfection of HeLa cells with RNA using the DEAE dextran method (Van der Werf et al, 1986). The sequence of the recovered virus was determined through the inserted region, and the non-plaque purified preparation had an $LD_{50}$ of greater than $10^6$ when tested in mice.

We claim:

1. An attenuated poliovirus in which there is a reversal of a base pairing in the part, or in a part corresponding to the part, of the 5' non-coding region of the genome of poliovirus type 3 Leon strain shown below:

```
      471     477     483
    ...UCC...CCAUGGA...
    ...AGG...GGUGCCU... .
      538     534     528
```

2. An attenuated virus according to claim 1, which is a type 1 poliovirus.

3. An attenuated virus according to claim 1, which is a type 2 poliovirus.

4. An attenuated virus according to claim 1, which is a type 3 poliovirus.

5. An attenuated virus according to claim 1, in which the bases at positions 472 and 537 of the genome of poliovirus type 3 Leon strain, or at positions corresponding to the said positions 472 and 537, are G and C respectively.

6. A process for the preparation of an attenuated poliovirus as defined in claim 1, which process comprises:

(i) introducing the or each desired mutation by site-directed mutagenesis into a sub-cloned region, which includes the or each position it is wished to mutate, of a cDNA of an a poliovirus;

(ii) reintroducing the thus modified region into the complete cDNA from which the region was derived; and (iii) obtaining live virus from the cDNA thus obtained.

7. A pharmaceutical composition comprising a pharmaceutically acceptable carrier or diluent and an attenuated virus as claimed in claim 1.

8. A method of vaccinating a patient against a poliovirus, which method comprises administering thereto an effective amount of a virus as claimed in claim 1.

9. An attenuated poliovirus having an attenuating mutation at least at a position which is, or corresponds with, position 537 of the genome of poliovirus type 3 Leon strain.

\* \* \* \* \*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

TTCGAAATTA ATACGACTCA CTATAGGCCT          30

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TATGACGCGT GCGGCCGCAA GCTTTAAAAC          30

( 2 ) INFORMATION FOR SEQ ID NO:3:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TTCGAAATTA ATACGACTCA CTATAGGTTA AAC          33

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CCATGGTTAG CATTAGCCGC          20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:5:

GGCUAAUCCU AACCAUGGAG    20

(2) INFORMATION FOR SEQ ID NO:6:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:6:

AGUCCGUGGC GGAACC    16